United States Patent [19]

Schulte et al.

[11] Patent Number: 4,636,194
[45] Date of Patent: * Jan. 13, 1987

[54] BURR-HOLE FLOW CONTROL VALVE

[75] Inventors: Rudolf R. Schulte; Gary P. East, both of Santa Barbara; Marga M. Bryant; Alfons Heindl, both of Goleta, all of Calif.

[73] Assignee: Pudenz-Schulte Medical Research Corp., Santa Barbara, Calif.

[*] Notice: The portion of the term of this patent subsequent to Dec. 24, 2002 has been disclaimed.

[21] Appl. No.: 796,299

[22] Filed: Nov. 8, 1985

Related U.S. Application Data

[63] Continuation-in-part of Ser. No. 575,165, Jan. 30, 1984, Pat. No. 4,560,375, which is a continuation-in-part of Ser. No. 510,381, Jun. 30, 1983, abandoned, which is a continuation of Ser. No. 208,514, Nov. 20, 1980, abandoned.

[51] Int. Cl.$^4$ .............................................. A61M 5/00
[52] U.S. Cl. ........................................... 604/9; 604/8
[58] Field of Search ...................... 604/8–10; 137/522

[56] References Cited

U.S. PATENT DOCUMENTS

| | | |
|---|---|---|
| 2,867,213 | 1/1959 | Thomas . |
| 2,933,102 | 4/1960 | Hillman et al. . |
| 3,111,125 | 11/1963 | Schulte . |
| 3,288,142 | 11/1966 | Hakim . |
| 3,492,996 | 2/1970 | Fountain . |
| 3,503,402 | 3/1970 | Schulte . |
| 3,527,226 | 9/1970 | Hakim . |
| 3,595,240 | 7/1971 | Mishler . |
| 3,601,128 | 8/1971 | Hakim . |
| 3,756,243 | 9/1973 | Schulte . |
| 3,758,073 | 9/1973 | Schulte . |
| 3,768,508 | 10/1973 | Schulte . |
| 3,769,982 | 11/1973 | Schulte . |
| 3,827,439 | 9/1974 | Schulte et al. . |
| 3,851,588 | 12/1974 | Taylor . |
| 3,980,097 | 9/1976 | Ellis . |
| 4,084,606 | 4/1978 | Mittleman . |
| 4,364,395 | 12/1982 | Redmond et al. . |
| 4,475,899 | 10/1984 | Muller .................................... 604/9 |
| 4,560,375 | 12/1985 | Schulte et al. ......................... 604/9 |

OTHER PUBLICATIONS

Brochure: The Surgical Treatment of Hydrocephalus–An Historical Review, Date: 1/1/81, Author: Robert H. Pudenz, M.D.
Brochure: Silastic Hydrocephalus Shunt, Date 12/72, Author: Dow Corning.
Brochure: Holter-Hausner International.
Brochure: CSF-Flow Control Shunts, Author: PS Medical.
Brochure: ACCU-Flor Valve System-Hydrocephalus Shunt Systems, Copyright: 1981, Author: Codman.

Primary Examiner—C. Fred Rosenbaum
Assistant Examiner—Gene B. Kartchner
Attorney, Agent, or Firm—Kelly, Bauersfeld & Lowry

[57] ABSTRACT

A surgically implantable flow control valve positionable over a burr-hole through a patient's skull is provided for use in shunt systems for controlling the release of entrapped body fluids. The valve includes a relatively rigid, unitized molded plastic base having a planar valve seat portion, an inlet passageway through the base which terminates at an inlet port situated within the planar valve seat portion of the base, a resilient membrane which is molded of a material different from the material of the plastic base and which is secured to the base in a manner surrounding and covering the inlet port, and an outlet separated from the inlet by the resilient membrane. Radiopaque indicators and markers are provided which permit a surgeon to ascertain specific information about the device and the functioning of the shunt system which would otherwise be unavailable without additional surgery.

19 Claims, 2 Drawing Figures

BURR-HOLE FLOW CONTROL VALVE

RELATED APPLICATIONS

This is a continuation-in-part of application Ser. No. 575,165, filed Jan. 30, 1984, now U.S. Pat. No. 4,560,375, which was a continuation-in-part of application Ser. No. 510,381, filed June 30, 1983 (now abandoned), which was a continuation of application Ser. No. 208,514, filed Nov. 20, 1980 (now abandoned).

BACKGROUND OF THE INVENTION

This invention relates generally the surgically implantable valves, and more particularly, to one-way flow control valves for controlling the flow of cerebrospinal fluid out of a brain ventricle and preventing backflow of fluid into the brain ventricle.

As is well known in the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart atrium.

Many such devices have been used heretofore, but prior devices have tended to become obstructed by particulate matter entering the drainage system or by the backward diffusion of blood into the system. Further, some prior devices have included moving parts which tended to adhere to other parts of the device and become immobile. When this occurs, the device itself becomes a barrier in the drainage system, and it adds to the problem it is intended to solve.

Moreover, manufacturers have been faced with a dilemma regarding the use of metal components in such valves. Some prior devices have included metal components which tended to interfere with x-ray photography and produce radiation scatter ("sunburst effect") on films taken by computerized axial tomography (CAT) scanning equipment, and such x-ray photography and CAT scanning frequently accompanies the use of surgically implanted flow control valves. It is desirable in some instances to be able to ascertain specific information from an implanted device by x-ray photography without having to reopen the patient's skin. For instance, it would be very desirable to provide an x-ray detectable marker which would facilitate detection of a separation of drainage tubing from the valve where doubt exists as to the integrity of an implanted shunt system.

Accordingly, there has been a long existing need in the medical arts for a convenient and effective device for controlling the flow of fluid from one part of the human body to another, which device is relatively inexpensive to manufacture and which can be constructed substantially of non-metallic parts which are not subject to adhering to one another and causing a malfunction of the device. As will become apparent from the following description, the present invention satisfies these needs and provides other related advantages.

SUMMARY OF THE INVENTION

The present invention resides in a device useful in shunt systems for controlling the flow of fluids from one part of the human body to another, which device is constructed substantially of non-metallic materials which prevent adhesion of one part to another, thereby providing trouble-free and reliable operation of the device. Moreover, the apparatus of the present invention is relatively inexpensive to manufacture, and can be easily modified to provide a variety of pressure/flow characteristics.

In general, and consistent with the disclosure in my co-pending U.S. patent application Ser. No. 575,165, the contents of which are incorporated by reference herein, the flow control valve of the present invention includes a rigid base having a planar surface, and a flow control member having a central support and a resilient membrane. The resilient membrane forms a releasable seal between its outer edges and the planar surface of the base, to prevent fluid flow from an inlet port situated on the base planar surface to an outlet separated from the inlet port by the resilient membrane. Although the resilient membrane is normally biased to prevent flow through the valve, it will open to permit fluid flow through the valve when the pressure upstream of the valve exceeds the pressure downstream of the valve by a predetermined amount.

More specifically with respect to the illustrated burr-hole flow control valve positionable upon a burr-hole through a patient's skull for controlling the flow of cerebrospinal fluid from the brain ventricles to another portion of the body, the base is of unitized construction and includes integral inlet and outlet connectors. An inlet passageway is provided through the inlet connector, and terminates at the inlet port situated on the base planar surface. A resilient dome overlies a portion of the base, including the base planar surface, to form a reservoir chamber. The outlet includes an outlet port in communication with the reservoir chamber which permits fluid flow thorough the outlet connector to exist the valve.

A variety of pressure/flow characteristics can be provided by the flow control valve of the present invention by providing such valves with different resilient membranes of varying thickness. The resistance to flow through the valves increases with an increase in membrane thickness.

In order to provide the desired resistance to adhesion between the base and the resilient membrane, particularly during storage of the valve, the unitized base is preferably formed of a polypropylene material and the membrane is preferably formed of a silicone elastomer material. Further the resilient dome which cooperates with the base to form the reservoir chamber is also preferably molded of a silicone elastomer material.

A radiopaque dot code, preferably situated on the dome, is provided to permit post-operative identification of the pressure/flow rating of the valve by x-ray photography. Furthermore, radiopaque markers are located on the connectors to allow verification of a valve to drain disconnect, by x-ray, if radiopaque surgical tubing separates from the valve after implantation of the system in the body.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
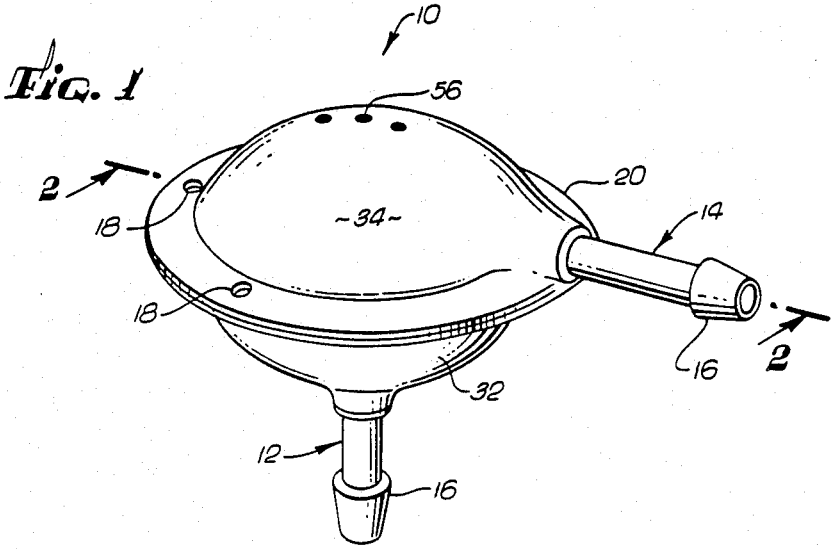
FIG. 1 is a perspective view of the burr-hole flow control valve of the present invention.

As shown in the drawings for purposes of illustration, the present invention is concerned with a burr-hole flow control valve, generally designated in the accompanying drawings by the reference number 10. This improved burr-hole flow control valve 10 is configured to be positionable upon a burr-hole formed through a patient's skull, and is intended for use in a surgically implanted shunt system for controlling the drainage of cerebrospinal fluid from the brain ventricles to another portion of the body. In order to connect the valve 10 in such a shunt system, the valve includes an inlet connector 12, which normally receives a proximal catheter (not shown), and an outlet connector 14, which receives one end of a piece of surgical tubing (not shown). The tube and catheter each slide over their respective connectors 12 or 14, and each is secured in place by a single ligature preferably tied just inside an annular ridge 16 formed near the end of each connector.

When the valve 10 is used in a drainage shunt system intended for treatment of hydrocephalus, the proximal catheter extends from the connector 12 into a brain ventricle containing cerebrospinal fluid under pressure, and the tube connected to the outlet connector 14 is a distal catheter which serves to discharge cerebrospinal fluid into, for example, the atrium portion of a patient's heart. Ordinarily, the valve 10 will be surgically implanted on the patient's skull immediately over the burr hole, with a flap of skin overlying the valve. To facilitate holding the valve 10 in its desired position after implantation, one or more suture holes 18 can be provided on a flange 20 surrounding a portion of the valve.

The burr-hole flow control valve 10 of the present invention provides a highly reliable valve design to prevent valve-seat deformation and membrane to seat sticking. The flow control valve of the present invention is inexpensive to produce and is designed to facilitate implantation by eliminating components to be connected or adjusted other than the proximal catheter and the surgical tubing of the shunt system. Also, the use of metal as a functional component of the improved valve 10 has been eliminated.

Figure 2:
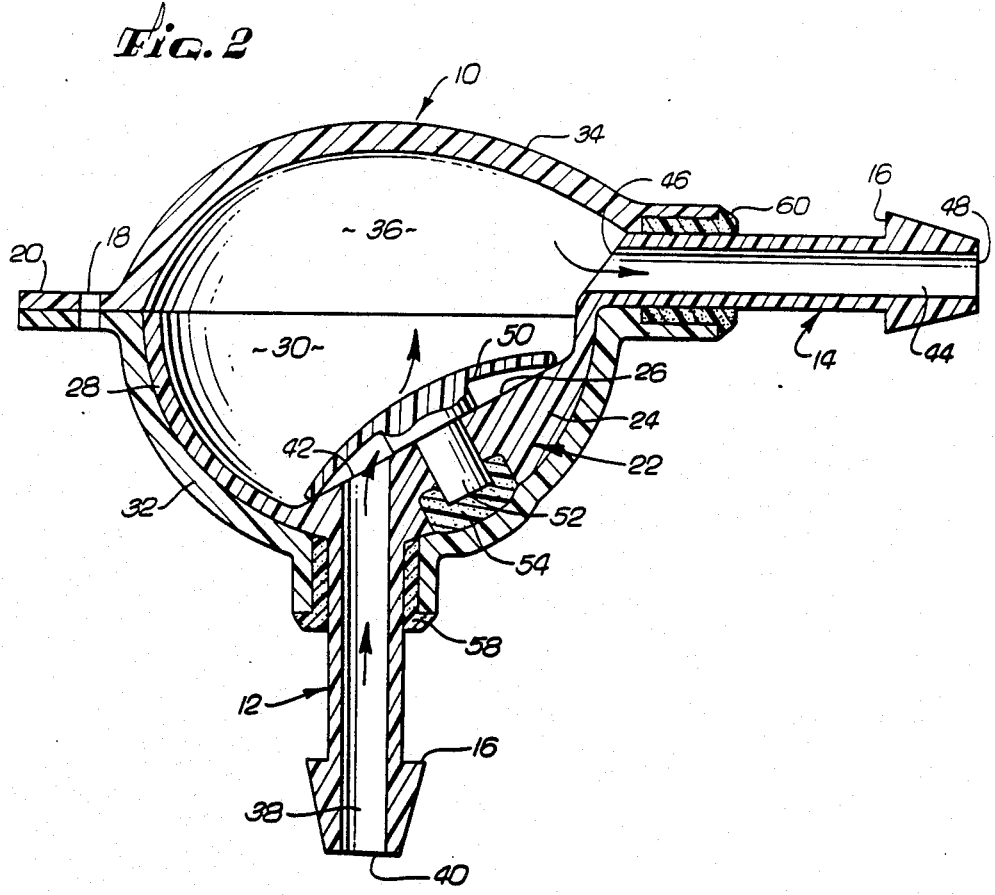
FIG. 2 is an elevational, sectional view of the flow control valve of the present invention, taken substantially along the line 2—2 of FIG. 1, and including arrows indicating the direction of fluid flow through the valve.

In accordance with the present invention, and as illustrated in FIGS. 1 and 2, the valve 10 is constructed to include a relatively rigid, unitized molded plastic base 22. This base 22 includes a valve supporting portion 24 having a planar surface 26, which valve supporting portion is integrally formed with the inlet and outlet connectors 12 and 14 (FIG. 2). The base 22 is constructed so that the planar surface 26 of the valve supporting portion 24 is surrounded by a semi-hemispherical portion 28 of the base which defines a well 30.

The base 22 is invested in a lower housing 32, through which the inlet connector 12 protrudes downwardly for placement through the burr-hole. This lower housing 32 sealingly engages about its periphery a resiliently flexible dome 34 to form a reservoir chamber 36 between the dome and the valve supporting portion 24 of the base 22.

An inlet passageway 38 through the valve 10 originates at an open end 40 of the inlet connector 12, and terminates an inlet port 42 situated on the planar surface 26. An outlet passageway 44 is also provided through the valve 10 which originates at an outlet port 46 in fluid communication with the reservoir chamber 36, and terminates at an open end 48 of the outlet connector 14. Fluid travelling through a shunt system utilizing the burr-hole valve of the present invention must thus first travel through the inlet passageway 38 to the reservoir chamber 36, and from there through the outlet passageway 44 before being allowed to move to another portion of the body.

The flow control valve 10 is arranged for controlling the flow of cerebrospinal fluid out of a brain ventricle and preventing backflow of fluid into the brain ventricle by the provision of a resilient non-metallic membrane 50. The membrane 50 is molded of a synthetic polymer material different from the material of the relatively rigid plastic base 22, and is secured to the base in a manner covering the inlet port 42 on the base planar surface 26. The resilient membrane 50 is normally biased to prevent communication between the inlet passageway 38 to the reservoir chamber 36, but will open to permit fluid flow (as indicated by the arrows in FIG. 2) when the pressure in the inlet passageway 38 exceeds the pressure in the reservoir chamber 36 by a predetermined amount. Moreover, should the pressure in the reservoir chamber 36 ever exceed the pressure in the inlet passageway 38, tending to cause flow in a reverse direction through the valve 10, the membrane 50 will seal tightly against the planar surface 26 and prevent any such reverse flow.

More specifically, the base 22 of the present invention is preferably formed of a polypropylene material, and the membrane 50 is formed of an elastomer material, preferably a silicon elastomer material. Both the polypropylene and elastomer materials have been shown to produce an acceptable level of tissue reaction, and it has been discovered that the use of this particular duality of materials, in contrast to the use of only a single material by the prior art, markedly decreases the chance of the membrane 50 adhereing to the base 22, which would clog the drain passage and defeat the purpose of the valve 10. Further, the valve of this invention is relatively inexpensive to manufacture, is trouble-free and reliable in use, and can be easily modified to produce a variety of pressure/flow characteristics.

An added advantage of using these particular materials is the avoidance of the negative effect of metal components, due to radiation scatter or "sunburst" effect, on films taken by, for example, computerized axial tomography (CAT) scanning equipment. This type of scanning frequently accompanies the use of surgically implanted flow control valves, and the absence or limitation of metal in the area scanned will permit more accurate and complete results to be gathered from CAT scanning.

The membrane 50 has an arch-shape, as for example a section of a sphere, and contacts the base planar surface 26 generally along the outer edges of the membrane in a manner surrounding the inlet port 42. The membrane 50 is secured to the valve supporting portion 24 of the base 22 by an upstanding central support 52 which is received in a mounting aperture in the base 22 and fixed thereto by an interference fit and use of an adhesive 54, or any other suitable means.

Since the valve 10 of the present invention is primarily designed to provide controlled resistance to cerebrospinal fluid flow from a brain ventricle, it will be appreciated that a doctor must be able to select a valve having the particular pressure/flow characteristics desired for each individual application. That is, a valve which permits flow at a relatively low pressure deferential may not be suitable where the maintenance of a higher pressure deferential is indicated. Toward this end, in order to provide a variety of valves having different pressure/flow characteristics, the valve 10 can be provided with a thick membrane 50 or a relatively thin membrane 50. Resistance to flow increases with the increase in membrane thickness.

The resilient dome 34 is also preferably molded of a silicone elastomer material, and is designed to permit injection into the drainage system or withdrawal of fluid samples by a hypodermic needle through the dome. In this regard, the base 22 provides a needle guard preventing passage of the needle all the way through the valve. Further, the dome 34 is sufficiently resilient to be deformed downwardly by external finger pressure. In this way, the flow control valve 10 can be flushed manually in the distal direction by simply manually depressing the dome 34.

On the upper surface of the dome 34, a radiopaque tantalum-impregnated silicone elastomer dot code 56 is situated to permit post-operative identification of the pressure/flow rating of the valve 10 by x-ray photography. An example of a useful code would be to utilize one dot to indicate a low pressure valve, two dots to indicate a medium pressure valve, and three dots to indicate a high pressure valve. Furthermore, radiopaque barium sulfate-impregnated markers 58 and 60 have been provided which wrap around a portion of the connectors 12 and 14. These radiopaque markers 58 and 60 provides means whereby a physician can detect a separation of the surgical tubing or proximal catheter from the valve 10 after implantation. Such valve/tubing disconnect is readily detectable in a shunt system through the use of x-ray photography when radiopaque surgical tubing or catheters are connected to the valve 10.

From the foregoing, it will be appreciated that the valve 10 provides a device by which the flow of cerebrospinal fluid out of a brain ventricle can be controled while preventing the backflow of fluid into the brain ventricle, and by which the chance of the valve clogging the drain passage can be greatly decreased. The valve 10 can be fabricated conveniently and economically, is trouble-free and reliable in use, provides convenient distal flushing of the shunt system, and can be easily adapted to provide a variety of pressure/flow characteristics. Further the inclusion of radiopaque indicators and markers provides the surgeon means for ascertaining specific information about the device and the functioning of the shunt system which would otherwise be unavailable without surgery.

While a particular form of the invention has been illustrated and described, it will be apparent that various modifications can be made without departing from the spirit and scope of the invention. Accordingly, the invention is not to be limited, except as by the appended claims.

We claim:

1. A surgically implantable flow control valve positionable upon a burr-hole through a patient's skull for controlling the flow of cerebrospinal fluid from the brain ventricles to another portion of the body, said valve comprising:
    a substantially rigid base of unitized construction including a valve supporting portion having a planar surface, an inlet connector integral with said supporting portion, and an outlet connector integral with said supporting portion, said supporting portion being situated within a protective well formed by said base;
    an inlet passageway through said base, said inlet passageway originating at an open end of said inlet connector and terminating at an inlet port situated on said planar surface;
    a resilient dome substantially overlying said valve supporting portion of said base to form a reservoir chamber therebetween, said dome having an arch-shape and being deformable toward said base by external pressure so that the extent of deformation is limited by contact between said dome and said base;
    an outlet passageway through said base, said outlet passageway originating at an outlet port in open communication with said reservoir chamber and terminating at an open end of said outlet connector;
    a flow control member including a central support and a resilient membrane, said central support being securely attached to said base and extending therefrom into said reservoir chamber to support said membrane, said membrane being generally arch-shaped and resiliently biased to contact said planar surface generally along the outer edges of said membrane in a manner surrounding said inlet port and forming a releasable seal between said planar surface and the outer edges of said membrane;
    an inlet radiopaque marker generally encircling a portion of said inlet connector;
    an outlet radiopaque marker generally encircling a portion of said outlet connector; and
    means for indicating the pressure/flow characteristics of said valve, said indicating means being x-ray detectable after implantation of said valve.

2. A surgically implantable flow control valve for controlling the flow of fluid from one portion of the human body to another, said valve comprising:
    a rigid base having a planar surface;
    a flow control member including a central support and a resilient membrane, said central support being securely attached to said base and extending therefrom to support said resilient membrane, said resilient membrane being generally arch-shaped and resiliently biased to contact said planar surface generally along the outer edges of said membrane in a manner forming a releasable seal between said planar surface and the outer edges of said membrane;

an inlet including an inlet port situated on said planar surface in a position surrounded by the releasable seal between said planar surface and the outer edges of said membrane;

an outlet separated from said inlet by said flow control member; and a flexible encasement generally surrounding said base.

3. A valve as recited in claim 2, including an inlet connector integral with said base, said inlet connector having a passageway therethrough forming said inlet.

4. A valve as recited in claim 3, including an outlet connector integral with said base, said outlet connector having an outlet passageway therethrough forming said outlet.

5. A valve as recited in claim 4, including an inlet radiopaque marker generally encircling a portion of said inlet connector, and an outlet radiopaque marker generally encircling a portion of said outlet connector.

6. A valve as recited in claim 2, wherein said encasement includes means for anchoring said valve in place when surgically implanted.

7. A valve as recited in claim 2, wherein said planar surface is situated within a protective well formed by said base, and wherein a resilient dome forming a portion of said flexible encasement substantially overlies said well to form a reservoir chamber in connection therewith, said dome having an arch-shape and being deformable toward said planar surface by external pressure.

8. A valve as recited in claim 2, wherein said base is formed of a molded plastic, and said membrane is molded of a non-metallic synthetic polymer material different from the material of said base.

9. A surgically implantable flow control valve for controlling the flow of fluid from one portion of the human body to another, said valve comprising:

a substantially rigid base of unitized construction including a valve supporting portion having a planar surface, an inlet connector integral with said supporting portion, and an outlet connector integral with said supporting portion;

an inlet passageway through said base, said inlet passageway originating at an open end of said inlet connector and terminating at an inlet port situated on said planar surface;

a flow control member including a central support and a resilient membrane, said central support being securely attached to said base and extending therefrom to support said membrane, said membrane being generally arch-shaped and resiliently biased to contact said planar surface generally along the outer edges of said membrane in a manner surrounding said inlet port and forming a releasable seal between said planar surface and the outer edges of said membrane;

an outlet passageway through said base, said outlet passageway originating at an outlet port separated from said inlet port by said flow control member, and terminating at an open end of said outlet connector; and a flexible encasement generally surrounding said base and including means for anchoring said valve.

10. A valve as recited in claim 9, wherein said encasement is deformable toward said planar surface by external pressure primarily for causing manual flushing of said valve.

11. A valve as recited in claim 10, wherein said encasement includes a resilient dome substantially overlying said valve supporting portion of said base to form a reservoir chamber therebetween.

12. A valve as recited in claim 9, wherein said base provides a protective well within which said resilient membrane is situated.

13. A valve as recited in claim 9, including an inlet radiopaque marker generally encircling a portion of said inlet connector.

14. A valve as recited in claim 9, including an outlet radiopaque marker generally encircling a portion of said outlet connector.

15. A valve as recited in claim 9, including means for indicating the pressure flow characteristics of said valve, said indicating means being x-ray detectable after implantation of said valve.

16. A valve a recited in claim 9, wherein said membrane is molded of a non-metallic synthetic polymer material different from the material of said base.

17. A valve as recited in claim 16, wherein said base is formed of a polypropylene material.

18. A valve as recited in claim 17, wherein said membrane is formed of an elastomer material.

19. A surgically implantable flow control valve for controlling the flow of fluid from one portion of the human body to another, said valve comprising:

a rigid base having a planar surface;

a flow control member including a central support and a resilient membrane, said central support being securely attached to said base and extending therefrom to support said resilient membrane, said resilient membrane being generally arch-shaped and resiliently biased to contact said planar surface generally along the outer edges of said membrane in a manner forming a releasable seal between said planar surface and the outer edges of said membrane;

an inlet including an inlet port situated on said planar surface in a position surrounded by the releasable seal between said planar surface and the outer edges of said membrane; and an outlet separated from said inlet by said flow control member;

wherein said planar surface is situated within a protective well formed by said base, and wherein a resilient dome substantially overlies said well to form a reservoir chamber in connection therewith, said dome having an arch-shape and being deformable toward said planar surface by external pressure.

* * * * *